US008263822B2

(12) United States Patent
Kang et al.

(10) Patent No.: US 8,263,822 B2
(45) Date of Patent: Sep. 11, 2012

(54) TREM-2 GENE AND PROTEIN AS INHIBITORS OF EXPRESSION OF GA733-2, AND TRANSGENIC ANIMALS COMPRISING THE SAME AND USES THEREOF

(75) Inventors: Hyung-Sik Kang, Gwangju (KR); Eun-Mi Kim, Gwangju (KR); Dong-Hern Kim, Yeosu-si (KR); Ha-Rim Choi, Gwangju (KR); Eun-Hee Lee, Gwangju (KR); Il-Soo Kim, Damyang-gun (KR); Chang-Eon Park, Gwangju (KR)

(73) Assignee: GLO Biotech (KR)

( * ) Notice: Subject to any disclaimer, the term of this patent is extended or adjusted under 35 U.S.C. 154(b) by 27 days.

(21) Appl. No.: 12/863,548

(22) PCT Filed: Feb. 18, 2009

(86) PCT No.: PCT/KR2009/000754
§ 371 (c)(1),
(2), (4) Date: Jul. 19, 2010

(87) PCT Pub. No.: WO2009/104889
PCT Pub. Date: Aug. 27, 2009

(65) Prior Publication Data
US 2010/0299767 A1    Nov. 25, 2010

(30) Foreign Application Priority Data
Feb. 22, 2008  (KR) .................. 10-2008-0016505

(51) Int. Cl.
*A01K 67/00*  (2006.01)
*A01K 67/027* (2006.01)
*A01K 67/033* (2006.01)
*G01N 33/00*  (2006.01)

(52) U.S. Cl. .................. 800/3; 800/13; 800/14; 800/18
(58) Field of Classification Search .................. None
See application file for complete search history.

(56) References Cited

U.S. PATENT DOCUMENTS
2005/0260670 A1  11/2005 Colonna et al.

FOREIGN PATENT DOCUMENTS
KR    10-2006-0135280   12/2006

OTHER PUBLICATIONS

Sigmund, C. (2000) Viewpoint: Are studies in genetically altered mice out of control? Arterioscler. Thromb. Vasc. Biology 20: 1425-1429.*
Wall, RJ (1996) Transgenic livestock: Progress and prospects for the future. Theriogenology 45: 57-68.*
Schmidt et al. (1990) The cytomegalovirus enhancer: a pan-active control element in transgenic mice. Molecular and Cellular Biology 10: 4406-4411.*
Isaiah R. Turnbull et al., "Trem-2 Attenuates Macrophage Activation," The Journal of Immunology, vol. 177, No. 6, Sep. 2006, pp. 3520-3524.
Kazuya Takahashi et al., "TREM2-Transduced Myeloid Precursors Mediate Nervous Tissue Debris Clearance and Facilitate Recovery in an Animal Model of Multiple Sclerosis," PLoS Medicine, vol. 4, No. 4, Apr. 2007, pp. 0675-0689.
Jessica A. Hamerman et al., "Cutting Edge: Inhibition of TLR and FcR Responses in Macrophages by Triggering Receptor Expressed on Myeloid Cells (TREM)-2 and DAP12," The Journal of Immunology, vol. 177, No. 4, Aug. 2006, pp. 2051-2055.
Kazuya Takahashi et al., "Clearance of apoptotic neurons without inflammation by microglial triggering receptor expressed on myeloid cells-2," The Journal of Experimental Medicine, vol. 201, No. 4, Feb. 21, 2005, pp. 647-657.
International Search Report—PCT/KR2009/000754 dated Sep. 22, 2009.
Baeuerle, et al., "EpCAM (CD326) finding its role in cancer," British Journal of Cancer 96: 417-423 (2007).
Cimino, et al., "Epithelial cell adhesion molecule (EpCAM) is overexpressed in breast cancer metastases," Breast Cancer Res Treat. 123(3): 701-708 (2010).
EPCAM epithelial cell adhesion molecule [*Homo sapiens*] Gene ID: 4072, updated on Jul. 31, 2011 http://www.ncbi.nlm.nih.gov/gene.
Mellstedt, et al., "Ga733/EpCAM as a Target for Passive and Active Specific Immunotherapy in Patients with Colorectal Carcinoma," Annals of the New York Academy of Sciences 254-262 (2006).
Munz, et al., "The Emerging Role of EpCAM in Cancer and Stem Cell Signaling," Cancer Research 69: 5627-5629 (2009).
Munz, et al., "The carcinoma-associated antigen EpCAM upregulates c-myc and induces cell proliferation," Oncogene 23: 5748-5758 (2004).
Osta, et al., "EpCAM is Overexpressed in Breast Cancer and Is a Potential Target for Breast Cancer Gene Therapy," Cancer Research 64: 5818-5824 (2004).
Schwartzberg, "Clinical experience with edrecolomab: a monoclonal antibody therapy for colorectal carcinoma," Critical Reviews in Oncology/Hematology 40: 17-24 (2001).
Trzpis, et al., "Epithelial Cell Adhesion Molecule More than a Carcinoma Marker and Adhesion Molecule," The American Journal of Pathology 171(2): (2007).
Zaloudik, et al., "Inhibition of tumor growth by recombinant vaccinia virus expressing GA733/CO17-1A/EpCAM/KSA/KS1-4 antigen in mice," Cancer Gene Therapy 9: 382-389 (2002).

* cited by examiner

*Primary Examiner* — Anne-Marie Falk
(74) *Attorney, Agent, or Firm* — Cantor Colburn LLP (57) ABSTRACT

Disclosed are a composition for inhibiting the expression of GA733-2 or for detecting GA733-2, which comprises TREM-2 gene or protein, a transgenic animal containing same, and a method using the same.

3 Claims, 6 Drawing Sheets

NO: No template

N/C: DNA (normal mouse genomic DNA)

P/C: Positive (plasmid DNA) control

Cell migration

Cell invasion

Control                TREM-2 transfection

SEQUENCE LISTING

<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Sense primer specific to TREM-2 gene

<400> SEQUENCE: 1
gaattcgccc ttggctggct gctggca                                      27

<210> SEQ ID NO 2
<211> LENGTH: 16
<212> TYPE: DNA
<213> ORGANISM: Artificial Sequence
<220> FEATURE:
<223> OTHER INFORMATION: Antisense primer specific to TREM-2 gene

<400> SEQUENCE: 2
gtacgtgaga gaattc                                                  16

<210> SEQ ID NO 3
<211> LENGTH: 21
<212> TYPE: DNA
<213> ORGANISM: Artificial Sequence
<220> FEATURE:
<223> OTHER INFORMATION: Sense primer specific to recombinant TREM-2
      gene

<400> SEQUENCE: 3
ccaagtctcc accccattga c                                            21

<210> SEQ ID NO 4
<211> LENGTH: 16
<212> TYPE: DNA
<213> ORGANISM: Artificial Sequence
<220> FEATURE:
<223> OTHER INFORMATION: Antisense primer specific to recombinant TREM-2
      gene

<400> SEQUENCE: 4
gtacgtgaga gaattc                                                  16

<210> SEQ ID NO 5
<211> LENGTH: 20
<212> TYPE: DNA
<213> ORGANISM: Artificial Sequence
<220> FEATURE:
<223> OTHER INFORMATION: Sense primer specific to GA733-2 gene

<400> SEQUENCE: 5
agagaaagcc cctacgacca                                              20

<210> SEQ ID NO 6
<211> LENGTH: 20
<212> TYPE: DNA
<213> ORGANISM: Artificial Sequence
<220> FEATURE:
<223> OTHER INFORMATION: Antisense primer specific to GA733-2 gene

<400> SEQUENCE: 6
gagaactcgg gtgccttttc                                              20

TREM-2 GENE AND PROTEIN AS INHIBITORS OF EXPRESSION OF GA733-2, AND TRANSGENIC ANIMALS COMPRISING THE SAME AND USES THEREOF

TECHNICAL FIELD

This invention relates to uses of triggering receptor expressed on myeloid cells 2 (TREM-2) gene and protein as inhibitors of the expression of GA733-2 antigen, and more specifically, to a composition and a method for inhibiting the expression of GA733-2 or for detecting GA733-2, comprising and using TREM-2 gene or protein, a transgenic animal containing the same, and methods using the same.

BACKGROUND ART

In 2003, WHO reported that approximately 22 millions of world population carry cancers. Cancers takes the second ranking (12%) next to cardiovascular diseases among all diseases in terms of the death rate with respect to the incidence rate. Especially, in advanced countries, the number of deaths due to cancers reaches about 2.5 million, accounting for about 21% of total deaths. In the future, it is expected that the incidence rate of cancers will rapidly increase by nearly 50% every year. In the Republic of Korea, the increase rate is about 10% a year, as of 2001. Before 1970s, most diseases in the Republic of Korea were caused by bacterial infections, insufficient nutrition, etc, however, incidence of cancers shows a tendency to increase continuously due to the economic growth and Westernized dietary life. Especially, it is known that colon cancer is more closely connected with the change of the dietary life than other cancers. At present, colon cancer increases at high speed and is a representative cancer, accounting for 11.2% of total cancers in the Republic of Korea.

GA733-2 (TACSTD1: tumor-associated calcium signal transducer 1, GenBank GeneID 4072) is a 40 kDa surface glycoprotein expressed in all epithelial cells. It is known to act as a homotypic calcium-independent cell adhesion molecule, and especially to be overexpressed in cancer cells. Especially, the amount of GA733-2 expressed in colon cancer cells remarkably differs from that in normal colon cells, as compared to other internal organ cells. A monoclonal antibody for GA733-2 is used for treating colon cancer.

In order to identify the cause of cancers, especially colon cancer, and to develop therapeutic agents therefor, the development of an animal model for controlling the expression of GA733-2 is necessary to perform experiments prior to clinical trials. In this regard, an animal model for inflammatory bowel disease (IBD) has been used as the model for colon cancer. However, an experimental mouse model for colon cancer to control the expression of GA733-2 has not yet been developed.

Meanwhile, it has been known in the art that TREM-2 (Triggering Receptor Expressed on Myeloid cells-2; Genbank Accession No. AK039477) plays a role of controlling the function of myeloid cells as a receptor transferring a signal via an adaptor protein DAP12. Moreover, in vitro experiments showed that TREM-2 derived from a microorganism suppresses an inflammatory reaction by inhibiting the expression of cytokines, suggesting that it involves in the immune regulation. However, it has not been clearly identified a role of TREM-2 in an immune system through in vivo experiments, since a probe for TREM-2 has not been developed.

The present inventors have found out that TREM-2 gene is specifically expressed with a high copy number only in progenitor cells of natural killer cells through serial analysis of gene expression (SAGE), and suggested that TREM-2 would have influence on differentiation into natural killer cells and activities thereof. Therefore, the inventors have cloned TREM-2 gene and manufactured a TREM-2-IgG fusion protein and filed a patent application therefor (Korean Patent Publication No. 2006-135280). However, it has never been known that TREM-2 involves in controlling the expression of GA733-2 associated with cancers, especially colon cancer. Further, a transgenic animal transformed with TREM-2, and capable of controlling the expression of GA733-2 has never been produced.

DISCLOSURE OF INVENTION

Technical Problem

The present inventors have performed extensive studies to develop a transgenic animal model controlling the expression of GA733-2, which is useful in the early diagnosis and the development of therapeutical agents for cancers, especially colon cancer. As a result, the inventors have unexpectedly revealed that TREM-2 gene, which is known to be involved in natural immunity, has an activity of inhibiting the expression of GA733-2.

Moreover, the present inventors have prepared a transgenic mouse overexpressing TREM-2 gene and confirmed that the expression of GA733-2 is inhibited in a tissue-specific manner in the transgenic mouse as compared to a wild-type mouse.

Accordingly, a first object of the present invention is to provide a composition for inhibiting the expression of GA733-2 antigen, in particular, for suppressing or treating colon cancer, which comprises TREM-2 gene or protein as an active ingredient.

A second object of the present invention is to provide a method for inhibiting the expression of GA733-2 antigen by using TREM-2 gene or protein.

A third object of the present invention is to provide a composition for detecting GA733-2 antigen, in particular, for diagnosing colon cancer, which comprises TREM-2 gene or protein as an active ingredient.

A fourth object of the present invention is to provide a method for detecting GA733-2 antigen, in particular, for diagnosing colon cancer, by using TREM-2 gene or protein.

A fifth object of the present invention is to provide a transgenic animal overexpressing TREM-2 gene, thereby inhibiting the expression of GA733-2 antigen.

A sixth object of the present invention is to provide a method for screening a suppressive or therapeutic agent for colon cancer by using TREM-2 gene or protein, or a transgenic animal containing the same.

A seventh object of the present invention is to provide a method for suppressing or treating colon cancer in a subject in need thereof by administering TREM-2 gene or protein to the subject.

An eighth object of the present invention is to provide a method for preparing a suppressive or therapeutic agent for colon cancer by using TREM-2 gene or protein.

A ninth object of the present invention is to provide a use of TREM-2 gene or protein for inhibiting the expression of GA733-2 antigen, in particular, for suppressing or treating colon cancer.

A tenth object of the present invention intends to provide a use of TREM-2 gene or protein for detecting GA733-2 antigen, in particular, for diagnosing colon cancer.

Technical Solution

A first aspect of the present invention provides a composition for inhibiting the expression of GA733-2 antigen, which comprises TREM-2 gene or protein as an active ingredient. The composition may be used as a suppressive or therapeutic agent of colon cancer.

A second aspect of the present invention provides a method for inhibiting the expression of GA733-2 antigen in a biological sample, which comprises adding TREM-2 gene or protein to the biological sample.

A third aspect of the present invention provides a composition for detecting GA733-2 antigen, which comprises TREM-2 gene or protein as an active ingredient. The composition may be used in the diagnosis, especially early diagnosis, of colon cancer.

A fourth aspect of the present invention provides a method for detecting GA733-2 antigen in a biological sample, which comprises adding TREM-2 gene or protein into the biological sample. The method may be used in the diagnosis, especially an early diagnosis of colon cancer.

A fifth aspect of the present invention provides a transgenic animal which is transformed with TREM-2 gene to overexpress it, thereby inhibiting the expression of GA733-2 antigen. The transgenic animal according to the present invention is preferably a transgenic mouse.

A sixth aspect of the present invention provides a method for screening a suppressive or therapeutic agent for colon cancer, which comprises;

adding a candidate to TREM-2 gene or protein, or a transgenic animal transformed with TREM-2 gene; and monitoring an effect of the candidate on the expression or activity of TREM-2 or GA733-2, and selecting the candidate enhancing the expression or activity of TREM-2 or inhibiting the expression or activity of GA733-2.

A seventh aspect of the present invention provides a method for suppressing or treating colon cancer in a subject in need thereof, which comprises administering an effective amount of TREM-2 gene or protein to the subject.

An eighth aspect of the present invention provides a method for preparing a suppressive or therapeutic agent for colon cancer, which comprises admixing TREM-2 gene or protein with a pharmaceutically acceptable carrier(s) or additive(s).

A ninth aspect of the present invention provides a use of TREM-2 gene or protein for inhibiting the expression of GA733-2 antigen, in particular, for suppressing or treating colon cancer.

A tenth aspect of the present invention provides a use of TREM-2 gene or protein for detecting GA733-2 antigen, in particular, for diagnosing colon cancer.

Advantageous Effects

TREM-2, as an inhibitor of the expression of GA733-2, and a transgenic animal model overexpressing TREM-2 thereby controlling the expression of GA733-2, in accordance with the present invention, may be useful for identification of the cause of cancers, especially colon cancer, as well as for the development of therapeutic agents or early diagnosis tools.

BRIEF DESCRIPTION OF DRAWINGS

The above and other aspects, features and advantages of the disclosed exemplary embodiments will be more apparent from the following detailed description taken in con-junction with the accompanying drawings in which.

BEST MODE FOR CARRYING OUT THE INVENTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise.

Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Figure 1:
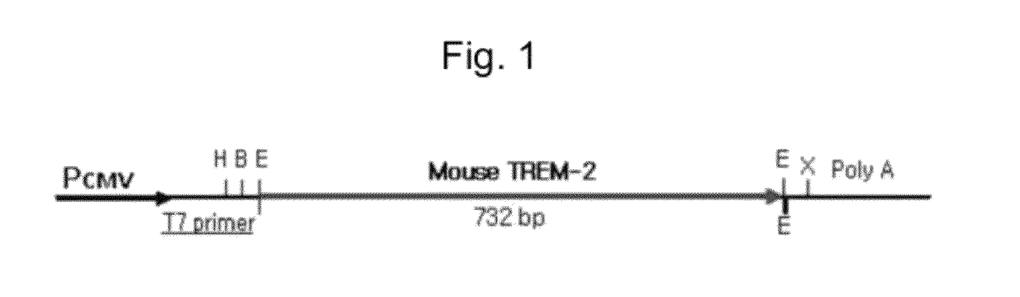
FIG. 1 shows a structure of the recombinant expression vector pcDNA3.1/TREM-2 according to the present invention.

Prior to the present invention, it has been known that TREM-2 involves in the immune regulation, but its ability to control the expression of GA733-2 antigen over-expressed in cancer cells, particularly, colon cancer cells has never been reported. In the present invention, a reverse transcription polymerase chain reaction (RT-PCR) is performed with TREM-2 specific primers for RNA isolated from mouse cell lines to amplify TREM-2 cDNA. The amplified product is cloned into pGEM-T vector and digested by EcoRI restriction enzyme, and then, cloned into an expression vector pcDNA3.1 to construct a recombinant expression vector pcDNA3.1/TREM-2 (see FIG. 1). A recombinant TREM-2 gene is purely isolated from the recombinant expression vector obtained. The purely isolated recombinant TREM-2 gene is microinjected into a fertilized egg of a mouse. The fertilized egg containing TREM-2 gene is implanted to an oviduct of a surrogate mother mouse to obtain a newborn mouse. Genomic DNA is isolated from a tail of the newborn mouse obtained.

Figure 2:
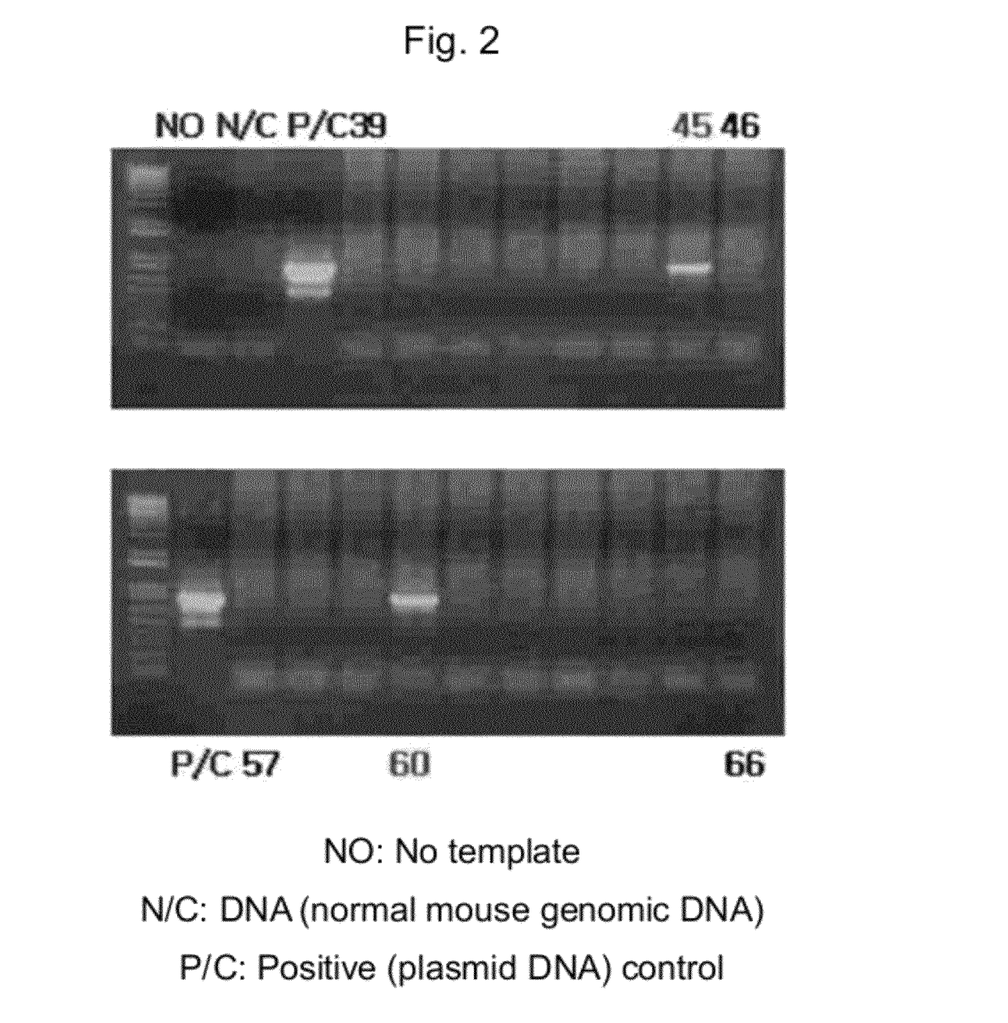
FIG. 2 is a photograph showing the insertion of pcDNA3.1/TREM-2 gene in the transgenic mouse transformed with TREM-2 gene according to the present invention through PCR.

Then, PCR is conducted with the DNA obtained as a template and primers specific to the recombinant gene, and the insertion of the recombinant gene is confirmed (see FIG. 2).

In accordance with the present invention, TREM-2 gene may be inserted to various animals except for human. For example, the animal may be a mouse, a rat, and the like. Preferred animal is a mouse.

In accordance with the present invention, TREM-2 gene may be inserted to a chromosome of an animal according to any conventional transformation methods well known in the art. Examples of the transformation methods include microinjection of a recombinant gene into a fertilized egg, use of a retroviral vector, or the like. Further, implantation of a fertilized egg containing a recombinant gene to a surrogate mother may be used. In terms of the safety of an operator, microinjection of a recombinant gene into a fertilized egg of an animal may be useful.

Further, in the present invention, the change of expression of GA733-2 gene in each tissue of TREM-2 transgenic mouse as compared to a wild-type mouse is confirmed by RT-PCR. As a result, an amount of the expression is remarkably changed, especially in thymus, Peyer's patches and lamina propria lymphocytes, most especially in lamina propria lymphocytes (see FIG. 3).

Figure 4:
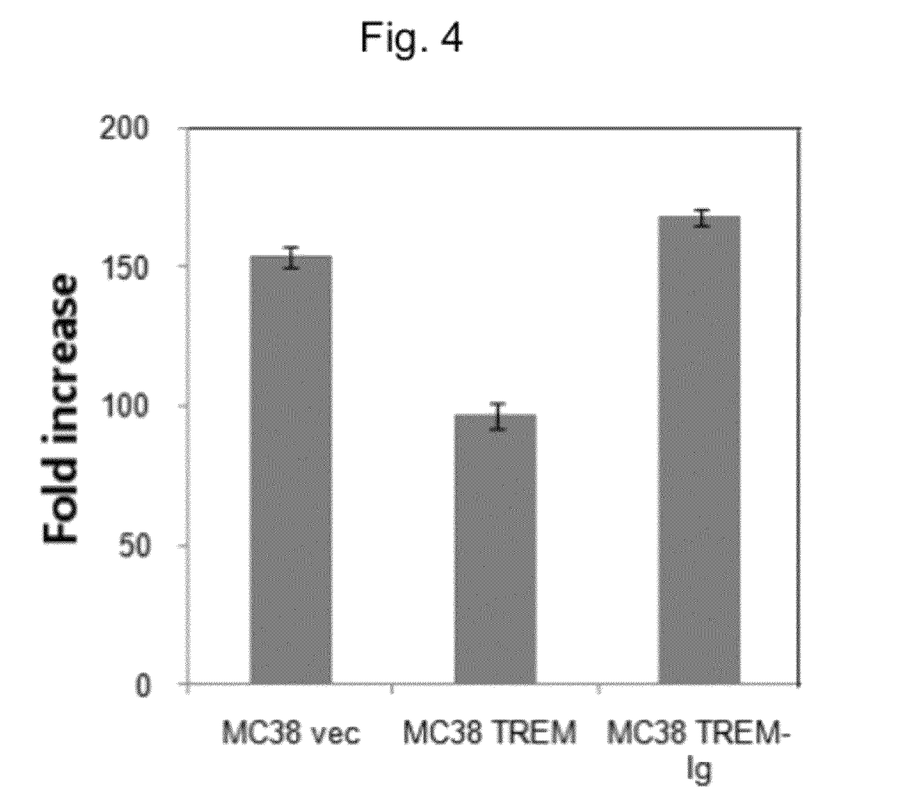
FIG. 4 is a graph showing the proliferation of colon cancer cells overexpressing TREM-2 gene, as compared to the control cells, as measured at 72 hours.
Figure 5:
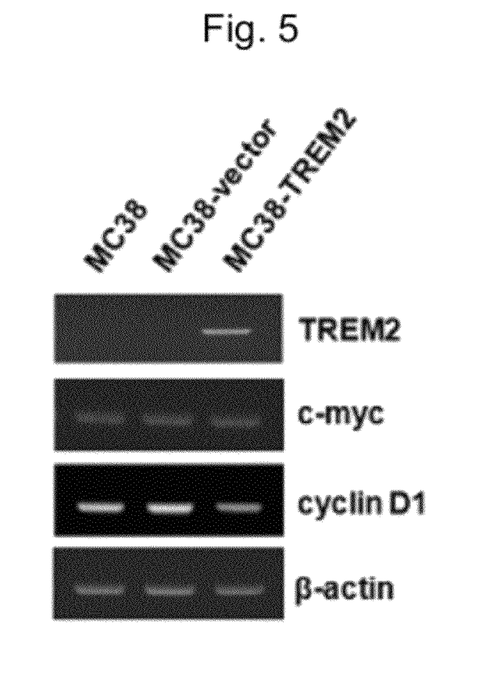
FIG. 5 is a photograph showing the change of expression of cell proliferation-related genes, in colon cancer cells overexpressing TREM-2 gene, as compared to the control cells.
Figure 8:
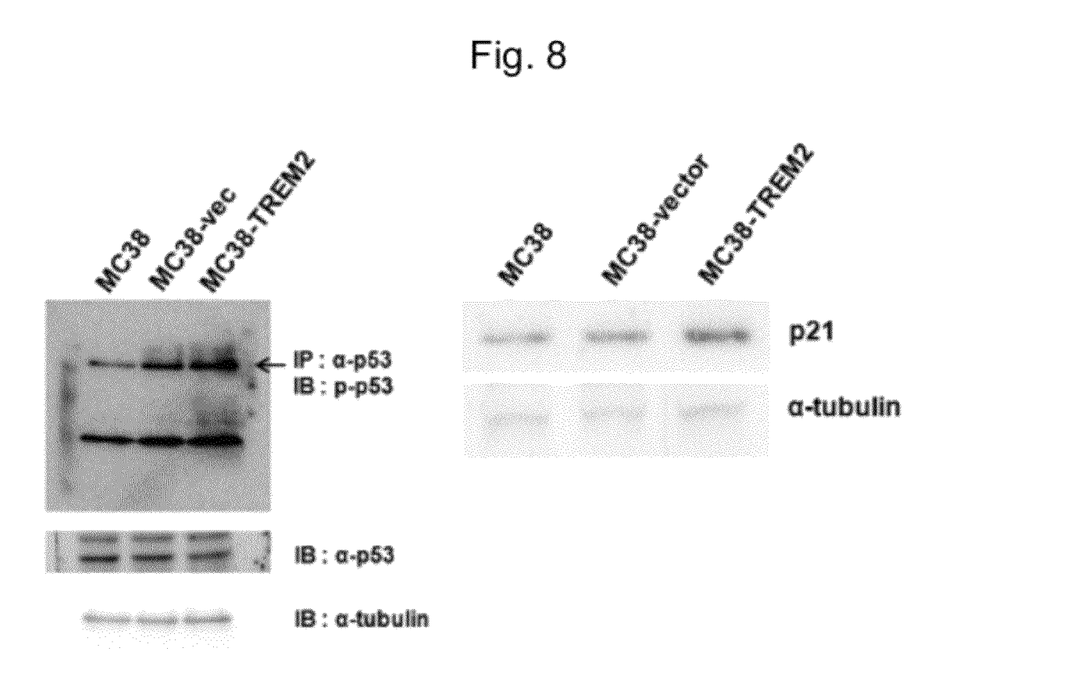
FIG. 8 is a photograph showing the change of expression of cell cycle-related genes, in colon cancer cells overexpressing TREM-2 gene, as compared to the control cells.

In addition, it is shown that TREM-2 decreases the proliferation of cells (see FIG. 4) and reduces the expression of the cell proliferation-related gene cyclin D1 while increasing the expression of tumor suppressor gene p21 (see FIG. 5). Further, TREM-2 controls the expression of Wnt signaling-related genes in a direction to decrease the proliferation of cells and induces the phosphorylation of p53, a cell cycle-related gene as well as a tumor suppressor gene, to increase the expression of p21 (FIG. 8). Also, TREM-2 decreases remarkably the migration and invasion of colon cancer cells (see FIG. 9) as well as reduces the expression of metastasis-related gene MMP9 (see FIG. 10), and the ability of natural killer cells to kill colon cancer cells is decreased depending on the ratio of effector cells to target cells (see FIG. 11).

From these results, it can be seen that TREM-2 gene has the activity of inhibiting the expression of GA733-2 overexpressed in cancer cells, especially colon cancer cells, and thus, is useful for the development of a diagnostic and therapeutic agent for cancers, especially for colon cancer.

In order to use the composition for inhibiting the expression of GA733-2 of the present invention as a therapeutic agent for cancers, especially for colon cancer, the dosage of TREM-2 gene or protein as an active ingredient may depend upon the age, sex and health condition of a subject to be treated, the kind and severity of the disease, and the like. For instance, it may be administered in an amount ranging from about 20 to 100 mg/kg body weight per time for an adult, and in a single dose or in divided doses, typically 2 to 3 times per day.

The composition of the present invention may be administered in any conventional administration routes well known in the art, for example, parenterally, especially by intravenous injection. The active ingredient of the present invention may be manufactured into formulations for oral administration such as tablets, hard or soft capsules, granules, chewable tablets, pills, powders, elixirs, suspensions, emulsions, solutions and syrups; or for parenteral administration such as aerosol, sachets, sterile injectable solutions and sterile powder, depending on the purpose of administration, as mixed with a pharmaceutically acceptable carrier(s) or additive(s). For oral administration, formulations such as tablets, capsules, granules, chewable tablets, pills, powders, elixirs, suspensions, emulsions, solutions and syrups comprising the active ingredient of the present invention may contain binders such as arabic gum, corn starch, micro-crystalline cellulose and gelatin; excipients such as calcium phosphate and lactose; disintegrators such as alginic acid, corn starches and potato starches; lubricants such as magnesium stearate; sweeteners such as sucrose and saccharin; and flavoring agents such as peppermint, methyl salicylate and fruit flavor. Capsules as unit dosage form may contain liquid carrier such as polyethylene glycol and fatty oil in addition to the ingredients mentioned above. Further, for parenteral administration, injectable solutions or suspensions may be administered subcutaneously, intravenously, intra-muscularly or intraabdominally. In general, injectable solutions or suspensions may be prepared by admixing homogeneously an effective amount of the active ingredient in a pharmaceutically acceptable liquid carrier(s) such as water, saline, aqueous dextrose and related sugar solution, non-volatile oil, ethanol, glycerine, glycols such as polyethylene glycol and propylene glycol, and the like. In addition, if necessary, an additive(s) such as antibacterial agents, chelating agents, buffers and preservatives may be contained. The pharmaceutically acceptable carriers or additives may be used, as long as they are pharmacologically inert and substantially non-toxic without inhibiting the activity of the active ingredients.

In case of using a gene as the active ingredient, the conventional gene therapy, for example, ex vivo and in vivo therapies, may be used and a vector for gene transfer may include, but are not limited to, retrovirus, adenovirus, adeno-associated virus, herpesvirus, and the like.

The composition according to the present invention, for example, to be used for detection and/or diagnosis, may be manufactured to the form of, for example, a microarray or chip. The microarray or chip of the present invention may be manufactured in accordance with any conventional methods well known in the art, for example, by immobilizing the active ingredient on a supports made of silica, semiconductors, plastics, gold, silver, magnetic molecules, polymers such as nylon, poly(dimethylsiloxane) (PDMS), cellulose or nitrocellulose, and the like, especially on glass slides.

Moreover, the transgenic animal overexpressing TREM-2 gene according to the present invention can inhibit the expression of GA733-2, and thus, the transgenic animal may be used as an animal model of cancers, especially colon cancer, for experiments prior to clinical trials. The transgenic mice transformed with TREM-2 may be useful for the identification of cause of cancer, especially colon cancer, and for the development of therapeutic agents or early diagnosis tools therefor.

MODE FOR THE INVENTION

The present invention will be more specifically explained with reference to the following examples, which are provided only for better understanding of the present invention, but should not be construed to limit the scope of the present in any manner.

Example 1

Preparation of Recombinant TREM-2 Gene

Pre-natural killer cells were directly isolated from C57BL/6 mouse to isolate RNA therefrom. Then, RT-PCR was performed with the RNA obtained as a template and TREM-2 specific primers [sense primer: 5'-GAATTCGC-CCTTGGCTGGCTGCTGGCA-3] (SEQ ID NO. 1) and anti-sense primer; 5'-GTACGTGAGAGAATTC-3'(SEQ ID NO. 2) to amplify TREM-2 cDNA.

PCR conditions were as follows: 30 cycles consisting of denaturation at 94° C. for 1 minute, annealing at 55° C. for 1 minute and extension at 72° C. for 1 minute.

The amplified PCR product was cloned into pGEM-T vector (Promega Co. U.S.A.) and digested with EcoRI restriction enzyme, and then cloned into an expression vector pcDNA3.1 (Invitrogen, U.S.A.) to construct a recombinant expression vector pcDNA3.1/TREM-2 (see FIG. 1). To purely isolate TREM-2 gene from the recombinant expression vector obtained, the bacteria derived region was cleaved and removed, and then, only the eukaryotic cell expressed region was dissolved in water for use in the subsequent step.

Example 2

Manufacture of TREM-2 Transgenic Mouse

The purely isolated recombinant TREM-2 gene obtained in Example 1 was microinjected into a fertilized egg of C57BL/6 mouse. The fertilized egg containing TREM-2 gene was implanted to an oviduct of a surrogate mother mouse to obtain a newborn mouse.

Example 3

Confirmation of Insertion of TREM-2 Gene in TREM-2 Transgenic Mouse

A tail of the newborn mouse obtained in Example 2 was cleaved and genomic DNA was isolated therefrom. Then, RT-PCR was conducted with the genomic DNA obtained as a template and TREM-2 specific primers [sense primer: 5'-CCAAGTCTCCACCCCATTGAC-3' (SEQ ID NO. 3) and anti-sense primer; 5'-GTACGTGAGAGAATTC-3' (SEQ ID NO. 4). PCR conditions were as follows: 35 cycles consisting of denaturation at 94° C. for 1 minute, annealing at 55° C. for 1 minute and extension at 72° C. for 1 minute.

The results are shown in FIG. 2. As shown in FIG. 2, it was confirmed that TREM-2 gene had been inserted to the transgenic mouse.

Example 4

Measurement of Expression of GA733-2 in Various Tissues of TREM-2 Transgenic Mouse Each tissue was isolated from TREM-2 transgenic mouse and then, investigated whether the expression of GA733-2 gene was controlled by TREM-2 gene in a tissue-specific manner. For this purpose, bone marrow, thymus, spleen, Peyer's patches (P.P TREM-2 gene specially controls) and lamina propria lymphocyte (LPL) were isolated from TREM-2 transgenic mouse and RT-PCR was performed with GA733-2 specific primers [sense primer: 5'-AGAGAAAGC-CCCTACGACCA-3' (SEQ ID NO. 5) and anti-sense primer; 5'-GAGAACTCGGGTGCCTTTTC-3' (SEQ ID NO. 6)]. PCR conditions were as follows: 35 cycles consisting of denaturation at 94° C. for 1 minute, annealing at 55° C. for 1 minute, and extension at 72° C. for 1 minute.

Figure 3:
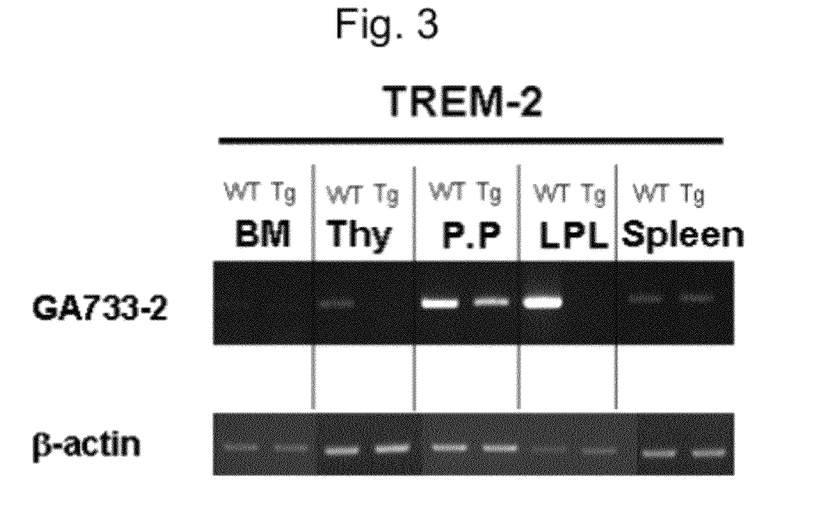
FIG. 3 is a photograph showing the change of expression of GA733-2 gene by TREM-2 gene in each tissue (bone marrow, thymus, spleen, Peyer's patches and lamina propria lymphocyte) of the transgenic mouse transformed with TREM-2 gene according to the present invention through RT-PCR.

The results are shown in FIG. 3. As shown in FIG. 3, the expression of GA733-2 gene in each tissue of TREM-2 transgenic mouse was tissue-specifically inhibited as compared to that of a wild-type mouse. Particularly, in thymus, Peyer's patches (PP) and lamina propria lymphocyte (LPL), most particularly, in LPL, the expression of GA733-2 gene was remarkably inhibited.

Example 5

Measurement of Colon Cancer Cell Proliferation Controlled by TREM-2 Gene 3-(4,5-dimethylthiazol-2-yl)-5(3-carboxymethonyphenol)-2-(4-sulfophenyl)-2H-tetra zolium (MTS) assay was performed to investigate the change of proliferation of colon cancer cells by TREM-2. The recombinant expression vector pcDNA3.1/TREM-2 was incorporated to colon cancer cells (MC-38, murine colon adenocarcinoma derived from C 57BL/6 mouse, Corbett T. H. et al., *Cancer Res.*, 35: 2434-2439, 1975) to overexpress TREM-2 gene, and then, the obtained cells were added to a 96 well microplate containing 100 μl of a culture medium. After culturing for 1 hour, the absorbance was measured at 490 nm and 655 nm. The results are shown in FIG. 4 (in FIG. 4, MC38 vector (vec) indicates the control group; MC38 TREM2 indicates the TREM-2 overexpression group; and MC38 TREM-Ig indicates the TREM-2-Ig fusion protein expression group). As shown in FIG. 4, the proliferation of colon cancer cells in the TREM-2 overexpression group decreased as compared to that in the control group.

Example 6

Measurement of Change of Expression of Colon Cancer Cell Proliferation-Related Genes by TREM-2 Gene In the control cells, colon cancer cells with pcNDNA3.1 vector introduced, and colon cancer cells with the recombinant expression vector pcDNA3.1/TREM-2 introduced to overexpress TREM-2, the expressions of the cell proliferation-related genes cMyc and cyclin D1, and tumor suppressor gene p21 were measured. The results are shown in FIG. 5 (wherein MC38 vector indicates the control group; and MC38-TREM2 indicates the TREM-2 overexpression group, applied to all other drawings below). As shown in FIG. 5, the overexpression of TREM-2 decreases the expression of cyclin D1 while increasing the expression of p21. Therefore, it can be seen that TREM-2 could control the expression of the cell proliferation-related genes.

Example 7

Figure 6:
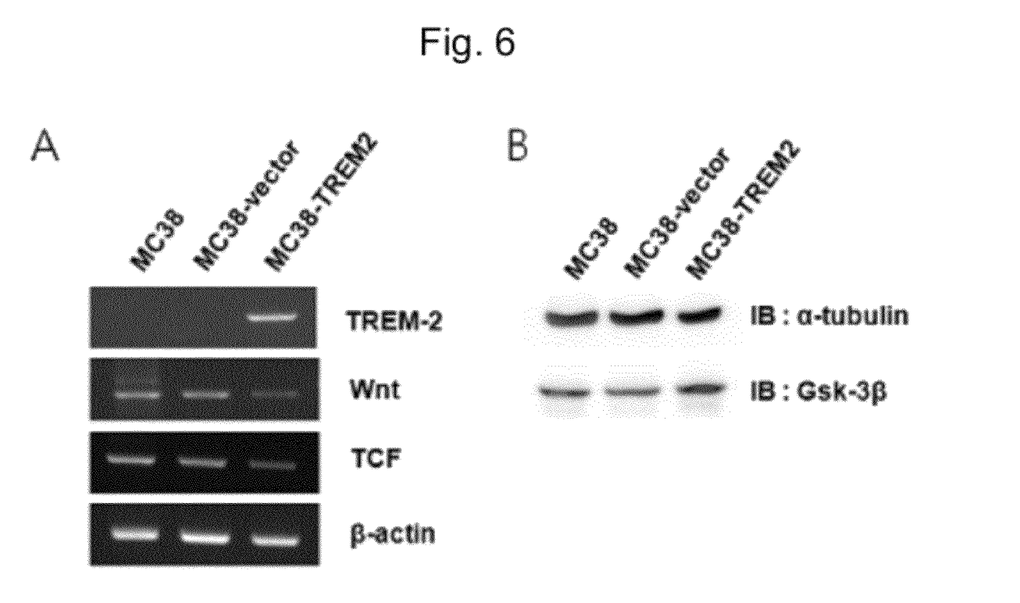
FIG. 6 is a photograph showing the change of expression of Wnt signaling-related genes, in colon cancer cells overexpressing TREM-2 gene, as compared to the control cells.
Figure 7:
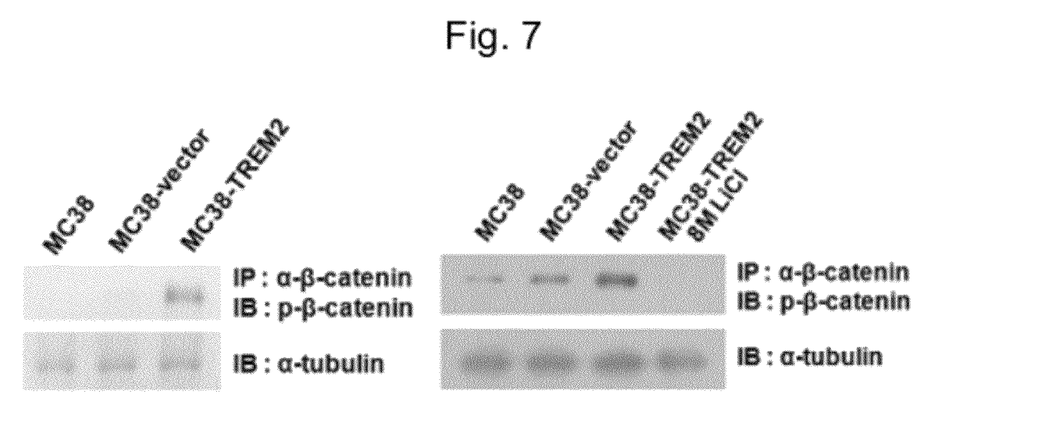
FIG. 7 is a photograph showing the change of the phosphorylation of -catenin among Wnt signaling-related genes, in colon cancer cells overexpressing TREM-2 gene, as compared to the control cells.

Measurement of Change of Expression of Wnt Signaling-Related Genes by TREM-2 Gene In the control cells, colon cancer cells with pcNDNA3.1 vector introduced, and colon cancer cells with the recombinant expression vector pcDNA3.1/TREM-2 introduced to overexpress TREM-2, the expressions of Wnt signaling-related genes, Wnt, GSK-3β and TCF, were measured. These results are shown in FIG. 6. As shown in FIG. 6, the overexpression of TREM-2 decreases the expression of Wnt and TCF while increasing the expression of GSK-3β as compared to the control group. Further, FIG. 7 shows the change of the phosphorylation of β-catenin by TREM-2. As shown in FIG. 7, the phosphorylation of β-catenin increases by increased GSK-3β. At the same time, the phosphorylation of β-catenin increased by TREM-2 was inhibited with the addition of lithium chloride, a GSK-3β inhibitor. Therefore, it can be seen that TREM-2 controls the expression of Wnt signaling-related genes in a direction to decrease cell proliferation.

Example 8

Measurement of Change of Expression of Cell Cycle-Related Genes by TREM-2 Gene

In the control cells, colon cancer cells with pcNDNA3.1 vector introduced, and colon cancer cells with the recombinant expression vector pcDNA3.1/TREM-2 introduced to overexpress TREM-2, the phosphorylation of p53, a cell cycle-related gene as well as a tumor suppressor gene, and the expression of p21 were measured. These results are shown in FIG. 8. From FIG. 8, it can be seen that TREM-2 increases the expression of p21 by inducing the phosphorylation of p53.

Example 9

Measurement of Migration of Colon Cancer Cells Controlled by TREM-2 Gene

Wound healing assay was performed to analyze an effect of TREM-2 on the migration of colon cancer cells. The control cells and the TERM-2 overexpressing colon cancer cells were spread, a wound was horizontally created thereon, and then, cell migration to the wounded region was observed.

Figure 9:
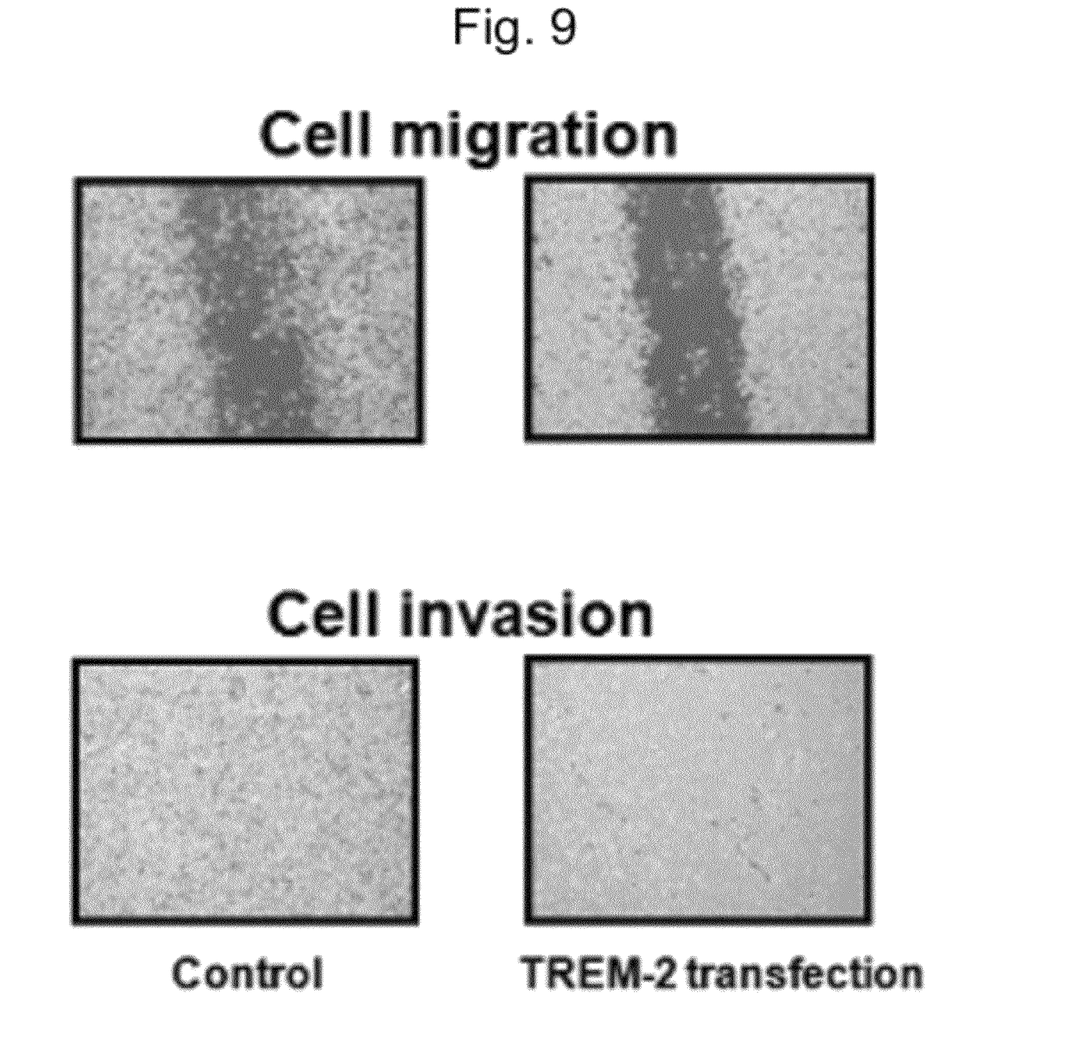
FIG. 9 is a photograph showing the migration of colon cancer cells overexpressing TREM-2 gene, as compared to the control cells.

The results are shown in the upper part of FIG. 9. As shown in FIG. 9 (upper part), the migration rate of the TERM-2 overexpressing colon cancer cells decreased remarkably.

Invasion assay, another method for analyzing the migration of cancer cells, was conducted. In this assay, the cells migrating from the upper chamber to the lower chamber bind onto an 8 μm pore polycarbonate filter. The bound cells were observed and photographed under a microscope. The results are shown in the lower part of FIG. 9. As shown in FIG. 9 (lower part), TREM-2 decreases the invasion rate of MC38 cell, as in the wound healing assay.

Example 10

Figure 10:
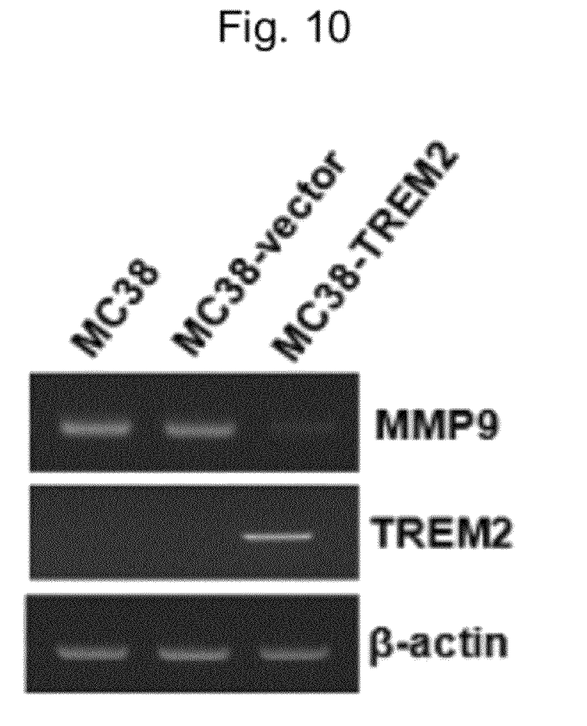
FIG. 10 is a photograph showing the change of expression of metastasis-related gene MMP9, in colon cancer cells overexpressing TREM-2 gene, as compared to the control cells.

Measurement of Change of Expression of Metastasis-Related Gene MMP9 by TREM-2 Gene In the control cells, colon cancer cells with pcNDNA3.1 vector introduced, and colon cancer cells with the recombinant expression vector pcDNA3.1/TREM-2 introduced to overexpress TREM-2, the expression of matrix metalloproteinase 9 (MMP9), a metastasis-related gene, was investigated. The results are shown in FIG. 10. As shown in FIG. 10, the overexpression of TREM-2 decreases the expression of MMP9.

Example 11

Figure 11:
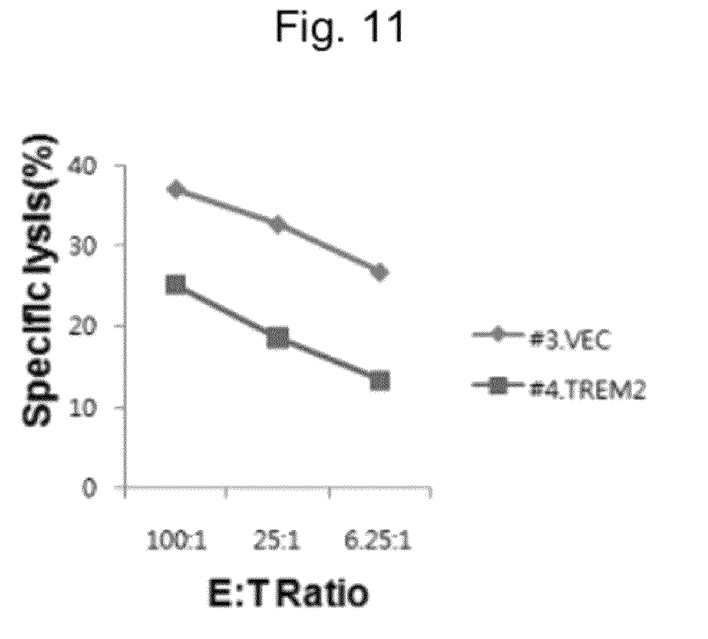
FIG. 11 is a graph showing the ability of natural killer cells activated by TREM-2 to kill colon cancer cells.

Analysis of Ability of Natural Killer Cells Activated by TREM-2 Gene to Kill Cancer Cells The colon cancer cells (target cells, T) with the recombinant expression vector pcDNA3.1/TREM-2 introduced to overexpress TREM-2 were labeled with 100 μCi of $^{51}$Cr for 2 hours and mixed with activated natural killer cells (effector cells, E) in a ratio of 1:6.25, 1:25 and 1:100 (the ratio of E:T), and then, reacted. After reaction for 4 hours, an amount of $^{51}$Cr released in the culture medium from the lysis of colon cancer cells by the natural killer cells was measured. The results are shown in FIG. 11. As shown in FIG. 11, the ability of the natural killer cells to kill colon cancer cells overexpressing TREM-2 decreases depending on the ratio of E:T as compared to the control colon cancer cell with pcNDNA3.1 vector introduced.

INDUSTRIAL APPLICABILITY

The present invention provides for the first time a use of TREM-2 as an inhibitor of the expression of GA733-2 associated with cancers, especially colon cancer, and a transgenic animal model overexpressing TREM-2, thereby controlling the expression of GA733-2. The invention will contribute to the identification of cause of cancers, especially colon cancer, as well as to the development of diagnosis, particularly, early diagnosis, tools and therapeutic agents therefor.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A transgenic mouse whose genome comprises a recombinant DNA sequence encoding TREM-2 protein operably linked to a promoter,
   wherein the transgenic mouse exhibits decreased expression of GA733-2 mRNA in cells of thymus, Peyer's patches and lamina propria lymphocytes as compared to a wild type mouse.

2. The transgenic mouse according to claim 1, which is a C57BL/6 transgenic mouse.

3. A method of screening a suppressive or therapeutic agent for colon cancer, which comprises;
   administering a candidate suppressive or therapeutic agent for colon cancer to a transgenic mouse whose genome comprises a recombinant DNA sequence encoding TREM-2 protein operably linked to a promoter, wherein the transgenic mouse exhibits decreased expression of GA733-2 mRNA in cells of thymus, Peyer's patches and lamina propria as compared to a wild-type mouse; and
   monitoring an effect of the candidate agent on expression of GA733-2 mRNA in Peyer's patches; and
   selecting the candidate agent inhibiting expression of GA733-2 mRNA,
   wherein the selected agent is a potential suppressive or therapeutic agent for colon cancer.

* * * * *